United States Patent [19]
Lippsmeier et al.

[11] 3,980,711
[45] Sept. 14, 1976

[54] PRODUCTION OF METHYLPHOSPHINE OXIDES

[75] Inventors: Bernd Lippsmeier, Hurth-Knapsack; Klaus Hestermann, Erftstadt Bliesheim; Gero Heymer, Erftstadt Liblar, all of Germany

[73] Assignee: Hoechst Aktiengesellschaft, Frankfurt am Main, Germany

[22] Filed: Feb. 12, 1975

[21] Appl. No.: 549,174

[30] Foreign Application Priority Data
Feb. 16, 1974 Germany............................ 2407460

[52] U.S. Cl..................... 260/606.5 P; 204/158 R; 204/158 HE
[51] Int. Cl.².............................................. C07F 9/02
[58] Field of Search .......... 260/606.5 P; 204/158 R, 204/158 HE

[56] References Cited
UNITED STATES PATENTS
3,309,408   3/1967   Moedritzer................. 260/606.5 P
3,732,316   5/1973   Lin............................. 260/606.5 P OTHER PUBLICATIONS
Hellmann et al., Ann. 659 pp. 49–63 (1962).
Buckler, J.A.C.S. vol. 82, pp. 4215–4220 (1960).

Trippett, J. Chem. Soc. pp. 2813–2816 (1961).

*Primary Examiner*—Helen M. S. Sneed
*Attorney, Agent, or Firm*—Connolly and Hutz

[57] ABSTRACT

Methylphosphine oxides of the general formula (I)

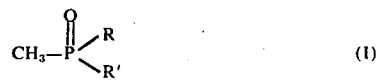

are produced from hydroxymethylphosphines of the general formula (II)

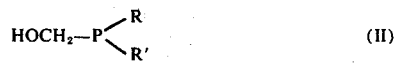

in which formulae R and R' each stand for identical or different alkyl-, cycloalkyl-, aralkyl- or aryl groups having from 1 to 18 carbon atoms, or carrying substituents being inert under the reaction conditions.

The methylphosphine oxides are more particularly produced by subjecting the hydroxymethylphosphines to a rearrangement reaction with the aid of radical-yielding compounds.

9 Claims, No Drawings

PRODUCTION OF METHYLPHOSPHINE OXIDES

The present invention relates to a process for making methylphosphine oxides of the general formula (I)

from hydroxymethylphosphines of the general formula (II)

in which formulae R and R' each stand for identical or different alkyl-, cycloalkyl-, aralkyl- or aryl groups having from 1 to 18 carbon atoms, preferably from 1 to 6 carbon atoms, more preferably from 1 to 2 carbon atoms, or carrying substituents being inert under the reaction conditions, or in which R and/or R' stand for $CH_2OH$-groups.

It is known (cf. Lieb. Ann. 659, pages 49 et seq. (1962) and U.S. Pat. No. 3,732,316) that hydroxymethylphosphines can be rearranged to isomeric methylphosphine oxides by heating them to high temperatures, over prolonged periods of time.

Disadvantages encountered in this known process reside in the fact that considerable energy is required to be used and in the fact that undesirable by-products are formed during the long heating periods at high temperatures. Only 40.5 % of isomeric dicyclohexyl-methylphosphine oxide is, for example, obtained by heating hydroxymethyl-dicyclohexylphosphine for 3 hours to temperatures within the range 240° and 250°C, while the principal reaction which actually occurs during that heat treatment is a cleavage reaction splitting the starting materials in formaldehyde and dicyclohexylphosphine. The formation of cleavage products, such as primary and secondary phosphines, is a further serious handicap, especially in view of the fact that phosphines having short carbon chains are partially self-ignitible in contact with air, and toxic.

We have now unexpectedly found that the above reaction can be effected under substantially simpler and milder conditions by subjecting the hydroxymethylphosphines to a rearrangement reaction with the aid of radical-yielding compounds.

The radical-yielding compounds which should conveniently be used include peroxy compounds, e.g. di-tertiary butyl peroxide, benzoyl peroxide, cyclohexyl peroxide, trifluoroperacetic acid or percarbonates, azo compounds, e.g. azo-bis-isobutyronitrile, or ultraviolet light or gamma rays.

The reaction should preferably be carried out under inert gas, e.g. under nitrogen, carbon dioxide or argon. It is also possible for the rearrangement reaction to be carried out in the presence of solvents or mixtures thereof, the preferred solvents being chloroform, methylene chloride, toluene or ethanol. The isomerization takes place at temperatures within the range −15° and 100°C, preferably within the range 25° and 75°C.

The rearrangement reaction may also be effected under pressure.

The resulting reaction product can be worked up, for example, by distillative separation of the solvent or by phase separation. Methyl phosphine oxides are valuable flameproofing agents and they find further use as intermediates in the production of flameproofing material, plant protecting agents and pharmaceutical preparations.

The process of the present invention provides a simple process for making methylphosphines of high purity in good yields.

EXAMPLE 1

108 g of bis-(hydroxymethyl)-methylphosphine was dissolved in 500 cc of chloroform. The whole was thoroughly mixed for 8 hours under nitrogen and irradiated with ultraviolet light. The reaction temperature was at 25°C. Once the reaction was terminated, the solvent was distilled off in known manner. 106 g of a distillation residue which was a colorless viscous oil was obtained. It crystallized gradually on standing and melted at 60°–65°C. Hydroxymethyl-dimethylphosphine oxide was obtained in a yield of 79 % of the theoretical, determined by gas-chromatography and NMR-spectroscopy. Titration with iodine in an acid medium indicated that the compound was free from trivalent phosphorus compounds.

The product can be further purified in known manner, e.g. be subjecting it to distillation under vacuum (principal fraction: $bp_{0.2\ mm\ Hg}$ 138°–140°C) or to fractional crystallization. In this case, a colorless, crystalline strongly hygroscopic product having a melting point between 74° and 77°C was obtained. The product so made was identical in all its chemical, physical and spectroscopic properties with a comparative product made in the manner described in German Patent Specification "Offenlegungsschrift" 2,060,217.

| | Analysis: $C_3H_9O_2P$ | | |
|---|---|---|---|
| | $^{31}$P-NMR: −53 ppm (ppm stands for parts per million) | | |
| | (as compared with the 85 % $H_3PO_4$ standard) | | |
| Calculated: | C 33.3 % | H 8.4 % | P 28.7 % |
| Found: | C 33.6 % | H 8.6 % | P 28.4 % |

EXAMPLE 2

108 g of bis-(hydroxymethyl)-methylphosphine was metered into 600 cc of methylene chloride with thorough agitation at 25°C, irradiation with ultraviolet light and under argon. The irradiation with ultraviolet light was continued for a further 5.5 hours. The solvent was distilled off and 107 g of a colorless oil was obtained, which crystallized gradually on standing. The crude product could not be found to have reducing properties with respect to iodine in an acid solution and was accordingly free from trivalent phosphorus compounds. $(CH_3)_2P(O)\ CH_2OH$ was obtained in a yield of 83 %, determined by gas-chromatography and NMR-spectroscopy. The product obtained by fractional distillation under vacuum had a melting point of 74°–75°C ($bp_{0.2\ mm\ Hg}$ 137°–139°C). It was identical with the product described in Example 1.

EXAMPLE 3

Example 1 was repeated save that the chloroform was replaced by a blend of toluene and methylene chloride (80:20 weight %) which was used at a temperature of 60°C. The result was the same as that described in Example 1.

EXAMPLE 4

108 g of bis-(hydroxymethyl)-methylphosphine was dissolved in 400 cc of ethanol. The whole was thoroughly agitated and a further 120 cc of ethanol containing 1 weight % of benzoyl peroxide was added thereto within 8 hours at 75°C, under nitrogen. The solvent was distilled off, after a post-reaction period of 4 hours at the boiling temperature of ethanol. 106.4 g of a residue which was hydroxymethyl-dimethylphosphine oxide of 78 % strength was obtained. The compound corresponded to that obtained in Example 1. It was further purified in known manner.

EXAMPLE 5

A stream of argon was passed over a period of 10 minutes at about 40°C through 600 cc of methylene chloride to completely expel dissolved oxygen therefrom. Following this, 100 g (1.09 mol) of hydroxymethyldimethylphosphine was added at room temperature under argon as a protective gas, with irradiation of ultraviolet light and thorough agitation. After the addition of phosphine was terminated, the whole was irradiated for a further 9 hours, and the solvent was distilled off. 106.8 g of a colorless solid residue was obtained of which 91.8 % was trimethylphosphine oxide, determined by NMR-spectroscopy. The impurities consisted substantially of bis-(hydroxymethyl)-dimethylphosphonium chloride and hydroxymethyl-trimethylphosphonium chloride together with minor quantities of starting material (less than 0.1 weight % after titration with iodine).

The crude product so obtained can be further purified in known manner by fractional distillation under vacuum, by sublimation or crystallization.

The product purified by sublimation under vacuum had a melting point within the range 139° and 140.5°C and was identical with a comparative product (mixed melting point, NMR and IR-spectrum) made from methyl magnesium chloride and phosphorus oxychloride (cf. Houben-Weyl, "Methoden der Organischen Chemie", 12/1, 158, 159 (1963)).

EXAMPLE 6

60 g (0.18 mol) of bis-(hydroxymethyl)-octadecylphosphine was dissolved under inert gas ($N_2$) in 600 cc of methylene chloride, which was completely freed from dissolved oxygen by flowing nitrogen therethrough, at the reflux temperature of the solvent. The whole was thoroughly mixed and irradiated with ultraviolet light for a total period of 9 hours at 25°C. The irradiation was terminated, the methylene chloride was distilled off and the residue was treated for a short while under the vacuum of a water jet pump. This was done so as to ensure the quantitative removal of solvent residues in the reaction product, if any. 61.2 g of a colorless highly viscous oil of which 80 % was hydroxymethyl-octadecyl-methylphosphine oxide, was obtained (NMR-spectroscopy). ($^{31}$P-NMR: −57 ppm). The product was free from trivalent phosphorus compounds (iodine titration in acid medium).

The product can be further purified by known methods, e.g. by crystallization or extraction.

EXAMPLE 7

100 g of tris-(hydroxymethyl)-phosphine was added to 600 cc of chloroform under nitrogen. The whole was agitated, heated to 55°C and irradiated with ultraviolet light for a total period of 9 hours at 50°C, with thorough agitation. Two phases were obtained which were separated from one another in a separator, after completion of the reaction and cooling. The upper phase (119.5 g) was treated for a short while under vacuum (2 mm of Hg; 15 minutes) to remove solvent adhering thereto, if any. 96.5 g of a slightly yellowish highly viscous oil was obtained. NMR-spectroscopy indicated that 74.1 % was bis-(hydroxymethyl)-methylphosphine oxide ($^{31}$P-NMR: −50 ppm). The lower phase was distillatively freed from chloroform and a further 3.1 g of rearrangement product was obtained. It can be further purified, if desired, by distilling it under mild vacuum or by recrystallization, for example from dimethyl formamide or an ethanol/isopropanol blend (Melting point: 68°–69°C).

We claim:

1. A process for making methylphosphine oxides of the general formula (I)

 (I)

from hydroxymethylphosphines of the general formula (II)

 (II)

in which formula R and R' each stand for identical or different alkyl-, cycloalkyl-, aralkyl- or aryl groups having from 1 to 18 carbon atoms,
or carrying substituents being inert under the reaction conditions, or in which R or R' stands for $CH_2OH$-groups, which process comprises subjecting the hydroxy-methylphosphines to a rearrangement reaction with the aid of radical forming agents selected from the group consisting of peroxy compounds, azo-compounds, ultra violet light and gamma rays.

2. The process as claimed in claim 1, wherein di-tertiary butylperoxide, benzoyl peroxide, cyclohexylperoxide, tri-fluoroperacetic acid or a percarbonate are used as peroxy compounds.

3. The process as claimed in claim 1, wherein azo-bis-isobutyronitrile is used as azo-compound.

4. The process as claimed in claim 1, wherein the rearrangement reaction is carried out under inert gas.

5. The process as claimed in claim 1, wherein nitrogen, carbon dioxide or argon is used as the inert gas.

6. The process as claimed in claim 1, wherein the rearrangement reaction is carried out in the presence of solvents or mixtures thereof.

7. The process as claimed in claim 1, wherein chloroform, methylene chloride, toluene or ethanol is used as the solvent.

8. The process as claimed in claim 1, wherein the rearrangement reaction is carried out at temperatures within the range −15° and 100°C.

9. The process as claimed in claim 1, wherein the rearrangement reaction is carried out at temperatures within the range 25° and 75°C.

* * * * *